(12) United States Patent
Na et al.

(10) Patent No.: US 9,072,782 B2
(45) Date of Patent: Jul. 7, 2015

(54) GADOLINIUM COMPLEX, METHOD FOR PREPARING SAME, AND MRI CONTRAST AGENT COMPRISING SAME

(75) Inventors: Kun Na, Bucheon-si (KR); Hyeon A Yim, Incheon (KR)

(73) Assignee: CATHLOIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 861 days.

(21) Appl. No.: 13/319,118

(22) PCT Filed: May 4, 2010

(86) PCT No.: PCT/KR2010/002819
§ 371 (c)(1),
(2), (4) Date: Nov. 16, 2011

(87) PCT Pub. No.: WO2010/128787
PCT Pub. Date: Nov. 11, 2010

(65) Prior Publication Data
US 2012/0058054 A1 Mar. 8, 2012

(30) Foreign Application Priority Data
May 7, 2009 (KR) .................. 10-2009-0039883

(51) Int. Cl.
*A61B 5/055* (2006.01)
*A61K 49/12* (2006.01)
*C08B 37/00* (2006.01)

(52) U.S. Cl.
CPC ........... *A61K 49/128* (2013.01); *C08B 37/0018* (2013.01)

(58) Field of Classification Search
CPC ..... A61K 49/00; A61K 49/12; A61K 49/128; A61P 35/00; C07H 1/00; C08B 37/0018
USPC .......... 424/1.11, 1.65, 1.73, 9.1, 9.2, 9.3, 9.4, 424/9.35; 534/7, 10–16; 536/123.1
See application file for complete search history.

(56) References Cited

U.S. PATENT DOCUMENTS 4,986,980 A * 1/1991 Jacobsen ............... 424/9.35

FOREIGN PATENT DOCUMENTS

| KR | 1020000076368 A | 12/2000 |
|---|---|---|
| WO | 2008094834 A2 | 8/2008 |

OTHER PUBLICATIONS

Guoying Sun et al., "Synthesis and evaluation of novel polysaccharide-GD-DTPA compounds as contrast agent for MRI", Journal of Magnetism and Magnetic Materials, vol. 265, Issue 2, Sep. 2003, pp. 123-129.
Thomas H. Helbich MD et al., "A new polysaccharide macromolecular contrast agent for MR imaging: Biodistribution and imaging characteristics", journal of Magnetic Resonance Imaging, vol. 11, Issue 6, pp. 694-701, Jun. 2000.
Sebastien Gouin et al., "Gadolinium Diethylenetriaminepentaacetic Acid Hyaluronan Conjugates: Preparation, Properties and Applications", Macromol. Symp. vol. 186, pp. 105-110, 2002.

* cited by examiner

*Primary Examiner* — D L Jones
(74) *Attorney, Agent, or Firm* — Novick, Kim & Lee, PLLC; Jae Youn Kim

(57) ABSTRACT

Disclosed are a gadolinium complex formed by coordination of gadolinium to the diethylenetriaminepentaacetic acid dianhydride (DTPA) moiety of a pullulan-DTPA conjugate formed by an ester bond between pullulan and DTPA, a preparation method thereof, an MRI contrast composition comprising the complex, and a method of providing information for diagnosis of disease using the complex as an MRI contrast agent. The pullulan-DTPA-Gd complex has a long in vivo half-life, low toxicity, and high MRI signal intensity resulting in clear MRI images, compared to prior gadolinium complexes, indicating that it is advantageously used as an MRI contrast agent. In addition, it is possible to obtain MRI images allowing one to differentiate between diseased liver tissue and normal liver tissue, indicating that it is used as an MRI contrast agent for the liver.

6 Claims, 4 Drawing Sheets

GADOLINIUM COMPLEX, METHOD FOR PREPARING SAME, AND MRI CONTRAST AGENT COMPRISING SAME

TECHNICAL FIELD

The present invention relates, in general, to a novel gadolinium complex, a preparation method thereof and an MRI contrast composition comprising the gadolinium complex. More particularly, the present invention relates to a novel gadolinium complex having low toxicity, a long half-life, and high MRI contrast ability for the liver, resulting from specific delivery, compared to gadolinium MRI contrast agents according to the prior art, and to a preparation method thereof and an MRI contrast composition comprising the gadolinium complex.

BACKGROUND ART

Contrast agents are frequently used to obtain images differentiated between a diseased tissue such as a tumor and the surrounding tissue, in order to make clearer the contrast between the tissues containing similar components, thereby observing the position, size or state of the diseased tissue. As a method for differentiating between a diseased tissue and the surrounding tissue as described above, magnetic resonance imaging (MRI) technology shows superiority and stability. Various methods making it possible to observe the inside of the body have been developed to date, and MRI technology was developed most recently, but the applicability or utility of MRI shows a tendency to increase rapidly, because MRI is safer than other imaging technologies. Methods such as X-ray radiography, CT and PET comprise administering to the human body a radioactive substance which has not been proven to be harmless to the human body, and for this reason, these methods cannot be applied to patients who can have a genetic mutation, particularly cancer patients or pregnant women. However, MRI can appear as an imaging technology that overcomes such shortcomings, including radioactivity and limitations on subjects to be applied.

MRI images can be viewed by the use of contrast agents. As used herein, the term "MRI contrast agent" refers to an agent that shortens the relaxation times (such as T1 and T2) of human tissues to increase the contrast of images. Main examples of the MRI agent include agents comprising paramagnetic or super-paramagnetic materials. Contrast agents can be used either to amplify the signal of the whole or partial tissue of a target organ or to weaken the signal of the surrounding tissue, thereby maximizing the contrast between light and shade.

MRI contrast agents can be largely divided into gadolinium contrast agents that are used as T1 contrast agents, and iron oxide (ferroxide or ferric oxide) contrast agents that are used as T2 contrast agents.

Gadolinium that is used mainly as a T1 contrast agent has a very low molecular weight and a very strong toxicity, which cause many problems when it is used as a contrast agent. For this reason, a DTPA-Gd complex (Magnevist™, Bayer) consisting of diethylene triamine pentaacetic acid coordinated with gadolinium was developed and is a paramagnetic MRI contrast agent which was first approved by the FDA. However, DTPA-Gd still has the problems of gadolinium. Specifically, it has a half-life which is as extremely short as about 14 minutes, such that it is rapidly discharged with urine after administration (Hiroki Yoshikawa et al., Gazoshindan, 6, 959-969 (1986)). Thus, it is difficult to diagnose several areas in the body by injecting it once. Also, it is delivered non-specifically to a normal tissue and a diseased tissue, thus making it impossible to obtain images having a clear contrast. In addition, although it has reduced toxicity compared to the element gadolinium, the toxicity thereof is still problematic. Moreover, because it has a molecular weight that slightly exceeds about 500 Da, which cannot overcome previous problems such as nonspecific delivery or a short half-life, it is difficult to use as a contrast agent for diagnosing lesions in the liver. In MRI, contrast time varies depending on the magnetic field intensity of an MRI spectrometer to be used, and thus in the case of low-magnetic-field MRI spectrometers which are generally widely used, contrast time should be long. Therefore, the DTPA-Gd complex, which has a short half-life and lacks selectivity for diseased tissues, has limitations as MRI contrast agents.

Iron oxide-based MRI contrast agents are used as T2 contrast agents and have an advantage in that they can show significant contrast effects even when they are used in very small amounts. However, they have a significant problem in that it is difficult to determine the kind of disease, even though information about the position of disease is transferred due to their strong signals. Ferucarbotran (Resovist™, Schering), a typical iron oxide-based contrast agent, is a super-paramagnetic contrast agent that is used for MRI imaging of the liver according to the basic principle by which it accumulates in liver tissue through the reticuloendothelial system. However, it is unclear that ferucarbotran can indeed be delivered specifically to the liver through the reticuloendothelial system so that it is effective in obtaining an accurate image for liver disease.

DISCLOSURE

Technical Problem

Accordingly, the present inventors have conducted studies to develop a contrast agent, which overcomes the problems of prior Gd-DTPA contrast agents, including a short half-life, toxicity, and non-specific delivery to diseased tissues, and, at the same time, allows high-contrast MRI imaging of liver disease, thereby completing the present invention.

It is, therefore, an object of the present invention to a compound that can be used as a contrast agent which has a sufficient half-life and low toxicity, can be delivered specifically to diseased tissue, and allows more effective imaging of liver disease.

Another object of the present invention is to provide a method for preparing said compound.

Still another object of the present invention is to provide an MRI contrast agent comprising said compound.

Yet another object of the present invention is to provide a method of using said compound as an MRI contrast agent to provide information for diagnosing disease.

Technical Solution

In order to accomplish the above objects, the present invention provides a gadolinium complex formed by coordination of gadolinium to the diethylenetriamine pentaacetic acid (DTPA) moiety of a pullulan-DTPA conjugate formed by an ester bond between pullulan and DTPA.

The gadolinium complex may be prepared by a method comprising the steps of: dissolving pullulan and DTPA in an organic solvent and allowing the solution to react so as to form an ester bond between the hydroxyl group of pullulan and DTPA, thereby preparing a pullulan-DTPA conjugate; and mixing an aqueous solution of the pullulan-DTPA conjugate with an aqueous solution of gadolinium and adjusting the mixed solution to a neutral pH, thereby forming a gadolinium complex.

The present invention also provides an MRI contrast agent comprising the gadolinium complex of the present invention.

The present invention also provides a method of providing information for diagnosis of disease using the gadolinium complex as an MRI contrast agent.

Hereinafter, the present invention will be described in further detail.

The present inventors have found that, if pullulan, a macromolecule having excellent biocompatibility, is conjugated by an ester bond to the DTPA moiety of a prior DTPA-Gd complex comprising gadolinium coordinated to DTPA, the resulting conjugate will have an increased in vivo half life and reduced toxicity when it is used as a contrast agent. In addition, the present inventors have found that a contrast agent having such pullulan conjugated thereto is primarily delivered through the liver, in which it is easily delivered to the reticuloendothelial system of normal liver tissue, but is not delivered to a diseased tissue (e.g., cancer) lacking the function of the reticuloendothelial system, such that MRI images allowing one to differentiate between diseased liver tissue and normal liver tissue can be obtained.

Thus, in one aspect, the present invention provides a gadolinium complex formed by coordination of to the diethylenetriamine pentaacetic acid (DTPA) moiety of a pullulan-DTPA conjugate formed by an ester bond between pullulan and DTPA.

Pullulan in the gadolinium complex (hereinafter also referred to as "pullulan-DTPA-Gd complex") according to the present invention is a water-soluble polysaccharide which is extracellularly produced by *Aureobasidium pullulans* called black yeast. Pullulan is a linear glucan of maltotriosyl units (each consisting mainly of 3 glucose units linked by α-1,4 linkages) linked by α-1,6 linkages. Pullulan is white amorphous powder which is tasteless and odorless, and it showed no problem as demonstrated from test results for various toxicities and mutagenicities, and was thus approved as a food in Japan. Unlike chemically synthesized general polymers, pullulan is a non-toxic polymer that is easily biodegraded by the pullulanase or isopullulnanase of intestinal bacteria into glucose. Thus, pullulan is a polymer recognized as a natural additive which is used in the preparation of thickeners, adhesives, stabilizers, biodegradable package materials, plastic binders, film-type oral rinses, etc.

Pullulan may have, for example, a structure represented by the following formula 2:

[Formula 2]

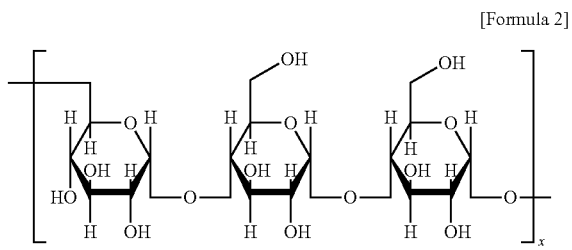

The above pullulan is a water-soluble natural polymer containing a plurality of highly reactive hydroxyl groups. Thus, it can form an ester bond with the carboxyl group of DTPA by simple mixing with DTPA in a suitable solvent, thereby forming a pullulan-DTPA conjugate. The pullulan that is contained in the gadolinium complex according to the present invention may have a molecular weight ranging from 500 to 500000.

DTPA that is contained in the gadolinium complex according to the present invention may be represented by the following formula 3:

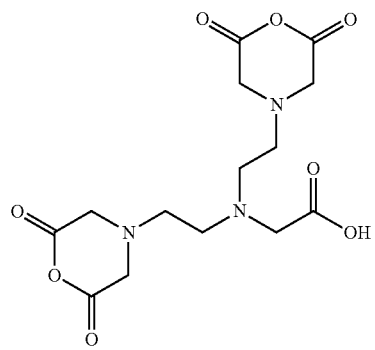 [SMILES: O=C(O)CN(CCN1CC(=O)OC(=O)C1)CCN1CC(=O)OC(=O)C1]

The above DTPA is in the form of a highly reactive dianhydride, and thus can easily form an ester bond with the hydroxyl group of pullulan. Also, it has a number of carboxyl groups, and thus can form a complex compound by coordination with gadolinium.

The DTPA can react with pullulan at various ratios to pullulan-DTPA conjugates. Preferably, 0.5-3 DTPA units may be conjugated to one maltotriosyl unit of pullulan. More preferably, one DTPA unit may be conjugated to one maltotriosyl unit of pullulan.

Most preferably, the gadolinium complex according to the present invention is a gadolinium complex represented by the following formula 1, wherein a pullulan-DTPA conjugate formed by an ester bond between one pullulan unit and one DTPA unit is coordinated with gadolinium:

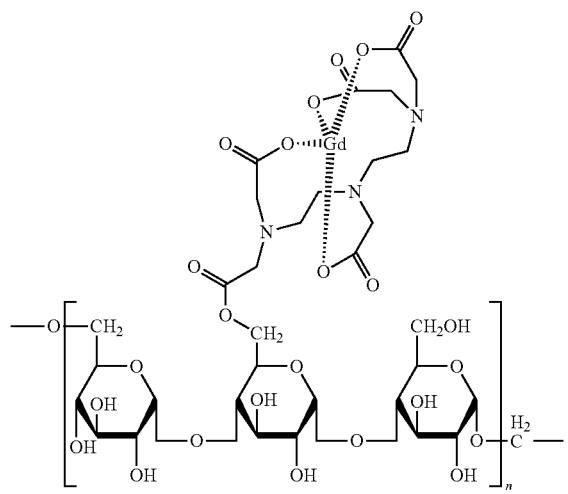

wherein n is an integer ranging from 1 to 1030.

In another aspect, the present invention provides a method for preparing the gadolinium complex according to the present invention, the method comprising the steps of: dissolving pullulan and DTPA in an organic solvent and allowing the solution to react so as to form an ester bond between the hydroxyl group of pullulan and DTPA, thereby preparing a pullulan-DTPA conjugate; and mixing an aqueous solution of the pullulan-DTPA conjugate with an aqueous solution of gadolinium and adjusting the mixed solution to a neutral pH, thereby forming a gadolinium complex.

In the step of preparing the pullulan-DTPA conjugate, the organic solvent that is used to dissolve pullulan and DTPA may be any organic solvent that can dissolve both pullulan and DTPA and does not interfere with forming the pullulan-DTPA by forming an ester bond between pullulan and DTPA. The organic solvent is preferably dimethyl sulfoxide (DMSO). The concentration at which pullulan and DTPA are dissolved in the organic solvent can influence the formation of the pullulan-DTPA conjugate. In the reaction for forming the pullulan-DTPA conjugate, pullulan and DTPA may be used at concentrations of $1\text{-}2.5 \times 10^{-2}$ mM and 5-15 mM, respectively. Most preferably, $1.7 \times 10^{-2}$ mM of pullulan and 10.5 mM of DTPA may be dissolved in DMSO (dimethyl sulfoxide) and allowed to react. At concentrations lower than the lower limits of the above concentration ranges, it will be difficult to form the pullulan-DTPA conjugate, and at concentrations higher than the higher limits of the above concentration ranges, pullulan and DTPA will aggregate with each other, rather than forming the pullulan-DTPA conjugate.

In the step of forming the gadolinium complex, the aqueous solution of the pullulan-DTPA conjugate is mixed with the aqueous solution of gadolinium, and the mixed solution is adjusted to a pH of 5-7, whereby gadolinium is coordinated to the DTPA moiety of the pullulan-DTPA conjugate, thereby forming the gadolinium complex. Herein, the mixed solution should be maintained at a pH of about 5-7 for about 24 hours or more. If this pH value is not maintained for about 24 hours or more, the complex will not be formed, and free gadolinium ions will be present, and thus toxicity caused by free gadolinium ions can cause very severe kidney troubles when the gadolinium complex is administered. As the gadolinium complex is formed, unreacted gadolinium can be removed by dialysis.

One embodiment of the above-described method for preparing the gadolinium complex according to the present invention is shown in the following reaction scheme 1:

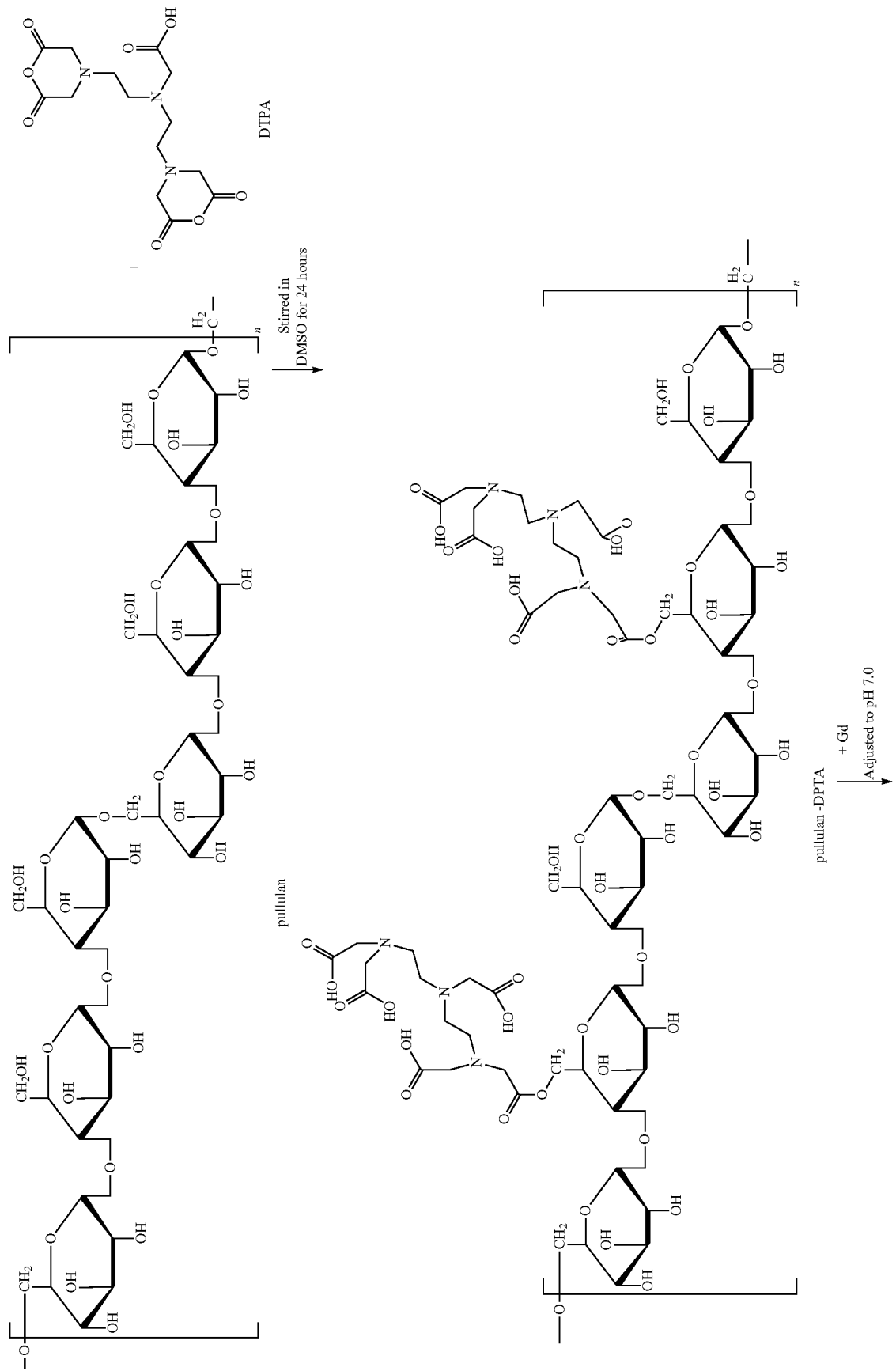

-continued
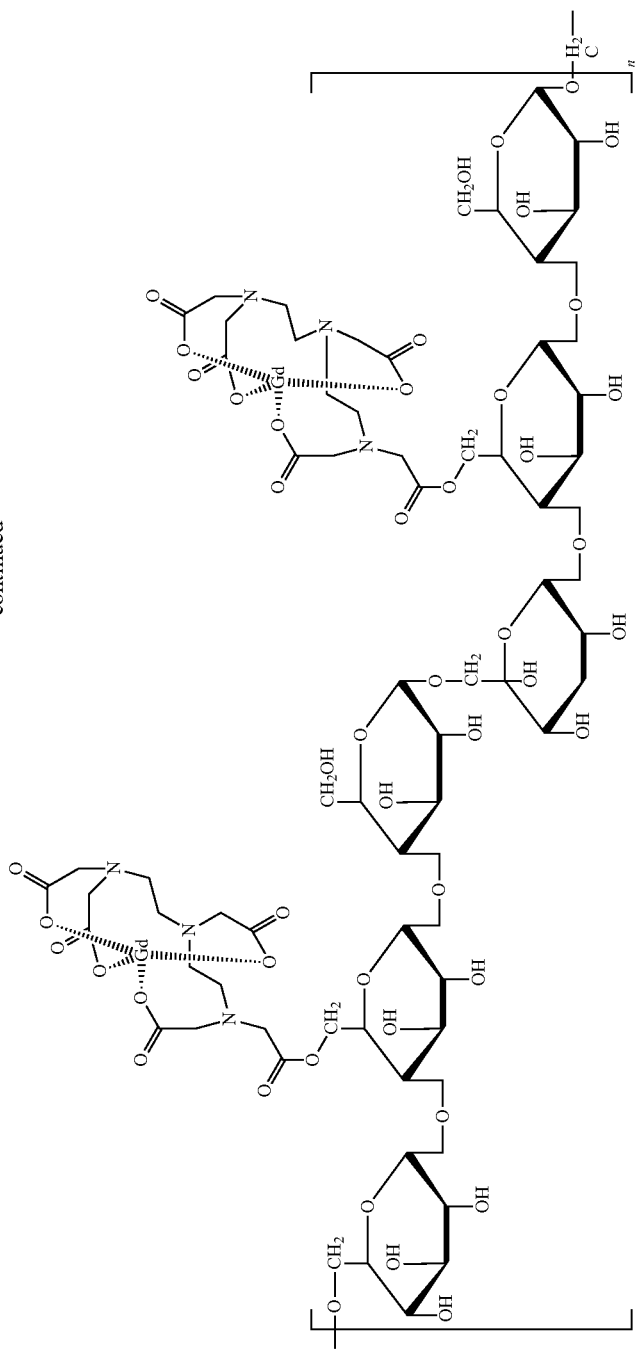

The gadolinium complex according to the present invention has an increased in vivo half-life and reduced toxicity compared to prior gadolinium complexes and is thus advantageously used as an MRI contrast agent. Also, the gadolinium complex according to the present invention is primarily delivered through the liver, in which it is easily delivered to the reticuloendothelial system of normal liver tissue, but is not delivered to a diseased tissue (e.g., cancer) lacking the function of the reticuloendothelial system, such that MRI images allowing one to differentiate between diseased liver tissue and normal liver tissue can be obtained, suggesting that the gadolinium complex can be used as an MRI contrast agent for the liver. In addition, the gadolinium complex according to the present invention remains in the liver for a long time without circulating through blood vessels, and thus shows a strong signal even when it is used in small amounts compared to prior approved gadolinium complexes, indicating that it may be used in small amounts compared to the prior gadolinium complexes. Such effects were demonstrated in Test Examples below. In Test Example 3 below, it was found that a gadolinium complex prepared according to an embodiment of the present invention showed a signal intensity which was about 7 times stronger than that of a control group. Also, in Test Example 4, a gadolinium complex prepared according to one embodiment of the present invention was administered to a rat having liver cancer, and then MRI imaging of the liver was carried out. As a result, it was found that the gadolinium complex continuously remained in the liver for 24 hours or more and that the contrast agent was delivered only to normal tissues other than the cancer tissue of the liver, whereby an image that was clearly different from that of the cancer tissue could be obtained.

Accordingly, in another aspect, the present invention provides an MRI contrast composition comprising the gadolinium complex according to the present invention. The MRI contrast composition can be used to obtain MRI images for diagnosis of diseases including cancer, for which prior gadolinium complexes could be used. Due to its advantages as described above, including an increased half-life, reduced toxicity and an increased contrast signal, it can be used more advantageously than prior gadolinium contrast agents. It is more notable that the contrast composition according to the present invention can be used as an MRI contrast agent for diagnosis of liver diseases, particularly liver cancer.

The contrast composition according to the present invention may be formulated according to a conventional formulation method for preparing contrast agents, known in the art. Preferably, it may be a formulation for intravenous injection. The contrast composition according to the present invention has a pH of about 6.0-8.0, and preferably 6.5-7.5. Also, the contrast composition according to the present invention may contain a physiologically acceptable buffer (e.g., 0.08% NaCl saline solution, or tris(hydroxymethyl)aminomethane) and physiologically acceptable additives (e.g., a stabilizer such as paraben).

The gadolinium complex in the contrast composition according to the present invention has blood residence time within the clinically effective range. The time taken for prior DTPA-Gd to be washed out from tissue is about 30 minutes, whereas the gadolinium complex in the contrast composition according to the present invention starts to be washed out from tissue at about 90 minutes or more after administration and remains in the liver up to about 24 hours, suggesting that the gadolinium complex according to the present invention has washing-out time suitable for use as a contrast agent. The dose of the contrast composition according to the present invention may vary depending on sex, age, bodyweight, human species and the kind of disease to be diagnosed. For adults, the contrast composition may be administered by intravenous injection at a dose of 0.0125-0.3 mmol/kg (on a gadolinium basis).

In still another aspect, the present invention provides a method of providing information for diagnosis of disease using the gadolinium complex according to the present invention as an MRI contrast agent. The gadolinium complex according to the present invention may be used as an MRI contrast agent in the same manner as prior gadolinium complexes, and thus can provide an MRI image as information for diagnosis of disease. In particular, the gadolinium complex according to the present invention can effectively provide information for diagnosis of liver diseases, particularly liver cancer.

Advantageous Effects

As described above, the pullulan-DTPA-Gd complex according to the present invention has a long in vivo half-life, low toxicity, and high MRI signal intensity resulting in clear MRI images, compared to prior gadolinium complexes, indicating that it can be advantageously used as an MRI contrast agent. In addition, it makes it possible to obtain MRI images allowing one to differentiate between diseased liver tissue and normal liver tissue, indicating that it may be used as an MRI contrast agent for the liver.

BEST MODE

Hereinafter, the present invention will be described in further detail with reference to examples. It is to be understood, however, that these examples are for illustrative purposes only and are not intended to limit the scope of the present invention in any way.

EXAMPLE 1

Preparation of Pullulan-DTPA Conjugate 150 mg of pullulan (TCI) and 300 mg of DTPA (diethylenetriaminepentaacetic acid dianhydride) were dissolved in 80 ml of dimethyl sulfoxide (DMSO) and allowed to react by stirring for 24 hours, thereby producing a pullulan-DTPA conjugate.

EXAMPLE 2

Preparation of Pullulan-DTPA-Gd Complex

The pullulan-DTPA conjugate prepared in Example 1 was dialyzed using a MWCO 3500 membrane for 3 days to remove the DMSO and was freeze-dried to remove water. 100 mg of the resulting pullulan-DTPA conjugate was dissolved in 24 ml of distilled water, a solution of 100 mg of gadolinium in 1 ml of water was added thereto, and then the resulting solution was adjusted to a pH of 7.0 with 1 N NaOH. Then, the pH of the solution was checked at 2-hour intervals, and when the pH did not significantly change between 5.0 and 7.0 for 24 hours, unreacted gadolinium was removed by dialysis using a MWCO 3500. After dialysis for about 1 day, the resulting material was freeze-dried to remove water, thereby obtaining the title complex.

TEST EXAMPLE 1

Confirmation (1) of Formation of Pullulan-DTPA-Gd Complex

In order to confirm whether an ester bond between pullulan and DTPA was formed in Example 1, pullulan, the pullulan-DTPA conjugate prepared in Example 1, and the pullulan-DTPA-Gd complex prepared in Example 2 were analyzed using FT-IR spectrometer spectrum 2000 (PERKIN ELMER). Specifically, each of pullulan, pullulan-DTPA and pullulan-DTPA-Gd was mixed with KBr at a ratio of 1:1 to make pellets, and the peak at a wavelength of 4000-400 nm was measured. The resulting FT-IR graphs are shown in FIG. 1.

Figure 1:
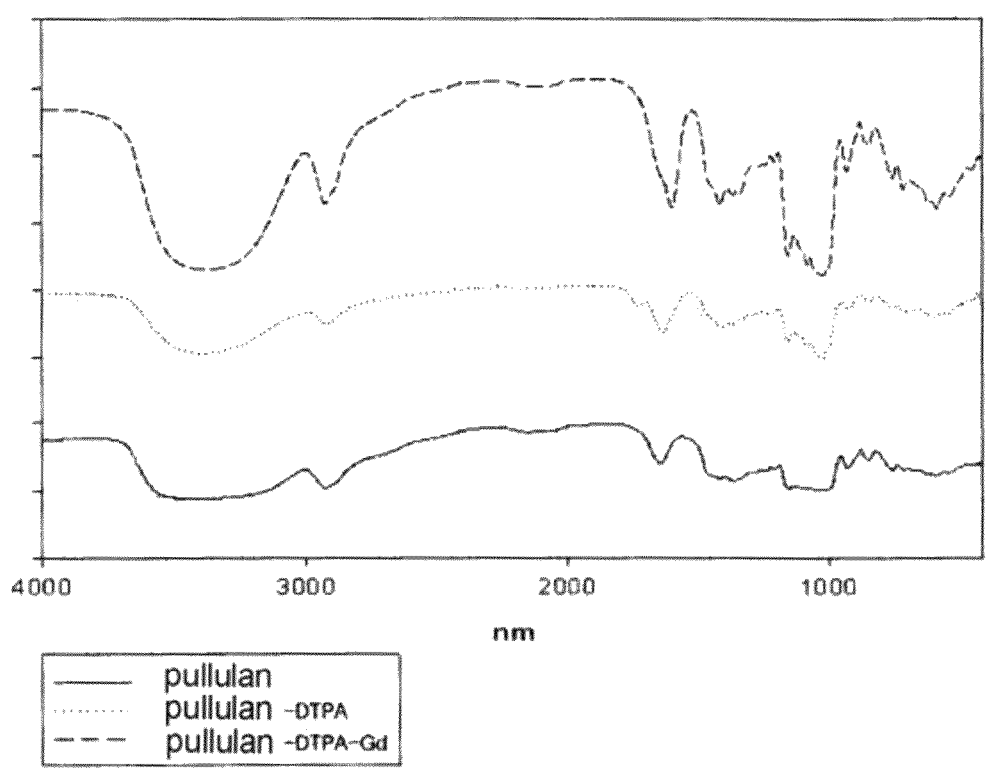
FIG. 1 is a set of graphs showing the results of Fourier transform infrared (FT-IR) spectroscopy of pullulan, a pullulan-DTPA conjugate, and a pullulan-DTPA gadolinium complex, prepared according to one embodiment of the present invention.

As can be seen in FIG. 1, the pullulan-DTPA conjugate showed new peaks at 1735 nm$^{-1}$ and 1150 nm$^{-1}$. Also, after it had formed a complex with gadolinium, the peaks slightly shifted back. This suggests that the desired compounds were prepared in Examples 1 and 2 above.

TEST EXAMPLE 2

Confirmation (2) of Formation of Pullulan-DTPA-Gadolinium Complex

During the synthesis processes in Examples 1 and 2 above, the zeta potential of each sample was measured, whereby the process in which the pullulan-DPTA-gadolinium complex was made was confirmed by a change in the zeta potential value. Specifically, 10 mg of each sample was dissolved in 1 ml of distilled water, and the surface charge of each sample was measured in triplicate. The zeta potential value measured for each of pullulan, pullulan-DTPA and the pullulan-DTPA-Gd complex is graphically shown in FIG. 2.

Figure 2:
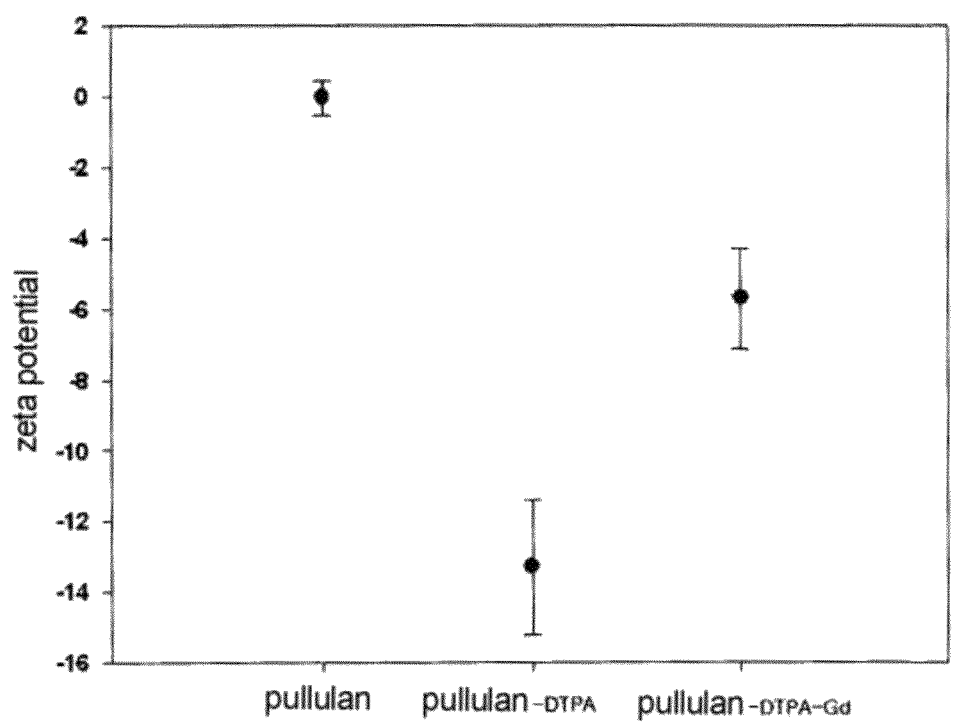
FIG. 2 is a set of graphs showing the results of measuring the zeta potentials of pullulan as a starting material, a pullulan-DTPA conjugate, and a pullulan-DTPA gadolinium complex (pullulan-DTPA-Ga), prepared according to one embodiment of the present invention.

As can be seen from the graphs in FIG. 2, pullulan had a value of substantially zero (0), but had a negative value after DTPA having a plurality of carboxyl groups has been conjugated thereto. Then, while it formed a complex with gadolinium having trivalent cations, the negative value decreased. This change can indicate that the desired compound was accurately made.

TEST EXAMPLE 3

Measurement of MRI Signal Intensity for Pullulan-DTPA-Gadolinium Complex

MRI signal intensity for the pullulan-DTPA-Gd complex prepared in Example 2 was measured using a 1.5 T MRI scanner (GE healthcare, USA). Specifically, the pullulan-DTPA-Gd complex was dissolved in 2 ml of distilled water at varying concentrations, and then each of the solutions was added to a 12-well plate, and the paramagnetic property at each concentration was measured.

Figure 3:
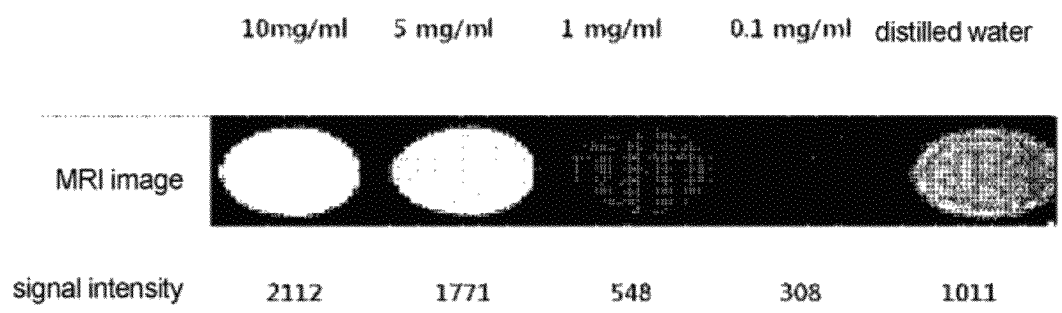
FIG. 3 shows the results of measuring a change in signal intensity as a function of concentration for a pullulan-DTPA gadolinium complex according to one embodiment of the present invention using a 1.5T magnetic resonance imaging scanner.

The results of the measurement are shown in FIG. 3.

As can be seen from the results in FIG. 3, 10 mg/ml of the pullulan-DTPA-Gd complex showed a signal intensity that was about 7 times higher than that of 0.1 mg/ml of the pullulan-DTPA-Gd complex. As shown in FIG. 3, the relative signal intensities of the samples were 1101 for DW and 2112 for the pullulan-DTPA-Gd complex.

TEST EXAMPLE 4

MRI Imaging of Liver Cancer

The pullulan-DTPA-Gd complex was administered to a rat having induced liver cancer at a dose of 0.05 mmol/kg (a gadolinium basis), after which the characteristics thereof in vivo were examined. Specifically, rat hepatoma N1S1 cells were injected directly into a rat at a cell density of $5 \times 10^5$ cells to make a liver cancer animal model. Then, the pullulan-DTPA-Gd complex was injected into the tail vein of the rat at a dose of 0.05 mmol/kg (a gadolinium basis). Then, MRI imaging of the rat liver was carried out using a 1.5 T MRI scanner (GE healthcare, USA). The results of the MRI imaging are shown in FIG. 4.

Figure 4:
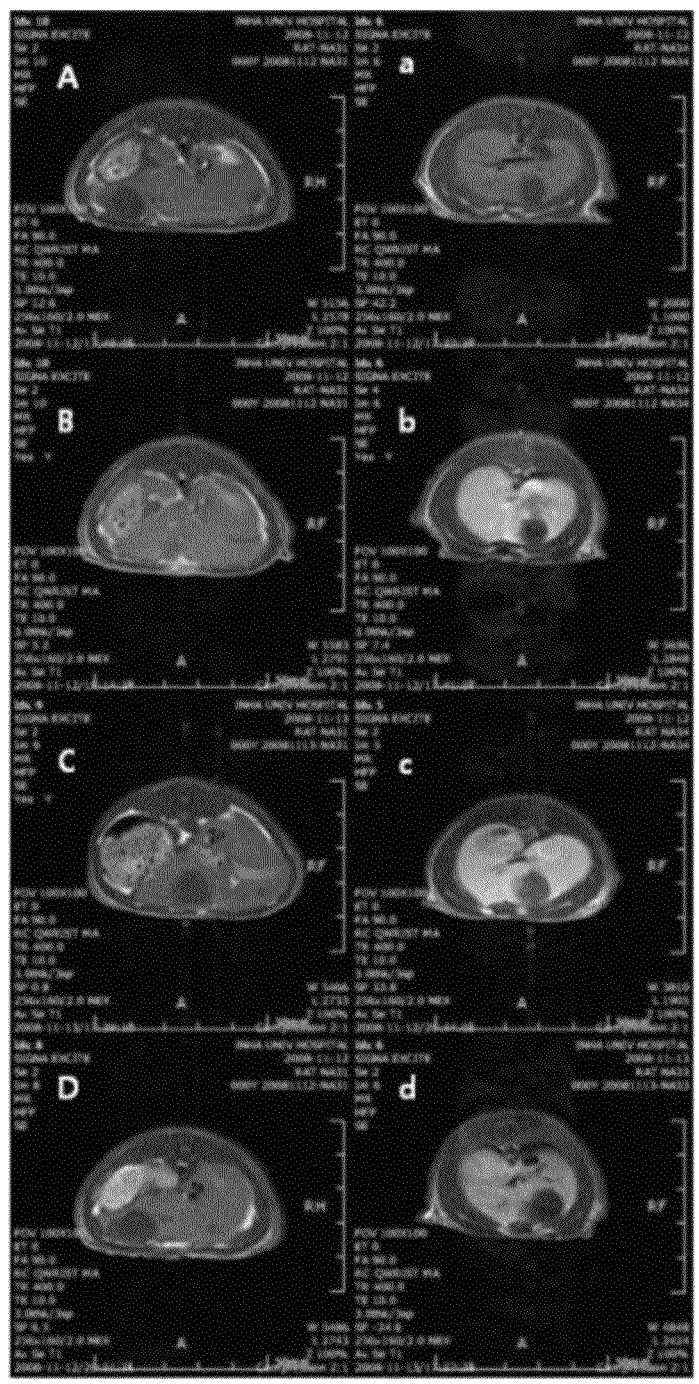
FIG. 4 is a set of MRI images taken at varying points of time after implanting cancer cells into the liver of a rate to induce liver cancer and injecting a pullulan-DTPA gadolinium complex according to one embodiment of the present invention into the tail vein of the liver cancer-induced rat at a dose of 0.05 mmol/kg.

As can be seen from the results in FIG. 4, the pullulan-DTPA-Gd complex according to the present invention continuously remained in the liver for 24 hours or more, and it was delivered only normal tissues other than the liver cancer tissue, so that an MRI image that was clearly different from that of the cancer tissue could be obtained.

The invention claimed is:

1. A method for preparing a gadolinium complex, the method comprising:

dissolving pullulan and DTPA in an organic solvent to produce a first solution: allowing the first solution to react so as to form an ester bond between a hydroxyl group of pullulan and DTPA to produce a pullulan-DTPA conjugate;

mixing an aqueous solution of the pullulan-DTPA conjugate with an aqueous solution of gadolinium to produce a mixed solution; adjusting a pH value of the mixed solution to 5-7;

maintaining the pH value of the mixed solution at 5-7 for at least 24 hours to substantially remove free gadolinium ions; and producing a gadolinium complex, wherein the gadolinium complex has a structure represented by Formula 1, wherein the pullulan-DTPA conjugate formed by an ester bond between one pullulan unit and one DTPA unit is coordinated with gadolinium:

Formula 1

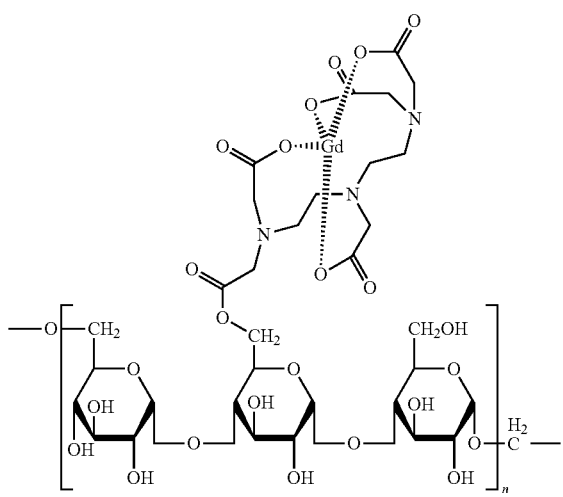

wherein n is an integer ranging from 1 to 1030.

2. The method of claim 1, wherein in the first solution a concentration of pullulan ranges from $1 \times 10^{-2}$ mM to $2.5 \times 10^{-2}$ mM and a concentration of DPTA ranges from 5 mM to 15 mM.

3. The method of claim 1, wherein the organic solvent is dimethyl sulfoxide (DMSO).

4. The method of claim 1, wherein the pH value of the mixed solution is adjusted using a 1 N NaOH solution.

5. The method of claim 1, wherein during the at least 24 hours period the pH value of the mixed solution is checked at 2-hour intervals.

6. The method of claim 2, wherein the concentration of pullulan is $1.7 \times 10^{-2}$ mM and the concentration of DPTA is 10.5 mM.

* * * * *